(12) United States Patent
Xu et al.

(10) Patent No.: US 9,402,391 B2
(45) Date of Patent: *Aug. 2, 2016

(54) STABILIZED OIL-IN-WATER EMULSIONS INCLUDING AGRICULTURALLY ACTIVE INGREDIENTS

(75) Inventors: Wen Xu, Cary, NC (US); Holger Tank, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 1005 days.

This patent is subject to a terminal disclaimer.

(21) Appl. No.: 12/400,451

(22) Filed: Mar. 9, 2009

(65) Prior Publication Data

US 2009/0247409 A1    Oct. 1, 2009

Related U.S. Application Data

(60) Provisional application No. 61/070,743, filed on Mar. 25, 2008.

(51) Int. Cl.
*A01N 37/18* (2006.01)
*A01N 25/04* (2006.01)
*A01N 25/10* (2006.01)
*A01N 25/30* (2006.01)
*A01N 25/22* (2006.01)

(52) U.S. Cl.
CPC ............ *A01N 25/04* (2013.01); *A01N 25/10* (2013.01); *A01N 25/30* (2013.01); *A01N 25/22* (2013.01)

(58) Field of Classification Search
USPC ........................................................ 504/363
See application file for complete search history.

(56) References Cited

U.S. PATENT DOCUMENTS

| 3,936,406 | A | * | 2/1976 | Rion ............................... 524/571 |
| 4,372,943 | A | | 2/1983 | Papanu et al. |
| 4,500,348 | A | | 2/1985 | Hausmann et al. |
| 4,997,642 | A | | 3/1991 | Curtis et al. |
| 5,846,905 | A | | 12/1998 | Frisch et al. |
| 6,074,986 | A | | 6/2000 | Mulqueen et al. |
| 6,296,864 | B1 | * | 10/2001 | Zen ................................. 424/405 |
| 2002/0098221 | A1 | | 7/2002 | Taranta et al. |
| 2007/0027034 | A1 | * | 2/2007 | Tank et al. .................... 504/363 |
| 2008/0090886 | A1 | | 4/2008 | Gottsche et al. |
| 2008/0171658 | A1 | | 7/2008 | Dyllick-Brenzinger et al. |
| 2009/0197768 | A1 | * | 8/2009 | Boucher et al. ............... 504/365 |
| 2009/0203528 | A1 | * | 8/2009 | Xu et al. ....................... 504/313 |

FOREIGN PATENT DOCUMENTS

| JP | 62-242601 | 10/1987 |
| JP | 5-25011 | 2/1993 |
| JP | 2007308440 A | 11/2007 |
| JP | 2007314515 | 12/2007 |
| WO | 0243488 | 6/2002 |
| WO | 2005046328 A | 5/2005 |
| WO | 2006094978 A | 9/2006 |
| WO | 2007/014386 | 2/2007 |
| WO | 2007/057028 | 5/2007 |
| WO | WO 2009/120486 | 8/2010 |

OTHER PUBLICATIONS

International Search Report of the International Searching Authority for PCT/US2009/036519, Jul. 24, 2009.
Written Opinion of the International Searching Authority for PCT/US2009/036519, Jul. 24, 2009.
International Preliminary Report on Patentability of the International Searching Authority for PCT/US2009/036519, Sep. 28, 2010.
English Translation of Shibuya Index—2007, Shibuya Index, Jun. 25, 2007, p. 118.

* cited by examiner

*Primary Examiner* — Ali Soroush
*Assistant Examiner* — Danielle Sullivan
(74) *Attorney, Agent, or Firm* — C. W. Arnett; Faegre Baker Daniels LLP

(57) ABSTRACT

The present invention relates to stable, agricultural oil-in-water emulsion compositions.

25 Claims, No Drawings

STABILIZED OIL-IN-WATER EMULSIONS INCLUDING AGRICULTURALLY ACTIVE INGREDIENTS

CROSS-REFERENCE TO RELATED APPLICATIONS

This Application claims the benefit of U.S. Provisional Application 61/070,743 filed on Mar. 25, 2008, which is expressly incorporated by reference herein.

FIELD OF THE INVENTION

The present invention relates to stable, agricultural oil-in-water emulsion compositions.

BACKGROUND AND SUMMARY

Concentrated oil-in water emulsions of liquid active ingredients or active ingredients dissolved in a solvent are commonly used in agricultural compositions due to certain advantages provided over other formulation types. Emulsions are water based, contain little or no solvent, allow mixtures of active ingredients to be combined into a single formulation and are compatible with a wide range of packaging material. However, there are also several disadvantages of such agricultural emulsions, namely that they are often complex formulations which require high amounts of surface-active agents for stabilization, are generally very viscous, have a tendency for Oswald ripening of the emulsion globules and separate over time. Therefore, improvements in such emulsion formulations are needed in the agricultural field.

Several oil-in-water emulsion compositions for cosmetics and dermatological applications have been described in patents U.S. Pat. No. 5,658,575; U.S. Pat. No. 5,925,364; U.S. Pat. No. 5,753,241; U.S. Pat. No. 5,925,341; U.S. Pat. No. 6,066,328; U.S. Pat. No. 6,120,778; U.S. Pat. No. 6,126,948; U.S. Pat. No. 6,689,371; U.S. Pat. No. 6,419,946; U.S. Pat. No. 6,541,018; U.S. Pat. No. 6,335,022; U.S. Pat. No. 6,274,150; U.S. Pat. No. 6,375,960; U.S. Pat. No. 6,464,990; U.S. Pat. No. 6,413,527; U.S. Pat. No. 6,461,625; and U.S. Pat. No. 6,902,737; all of which are expressly incorporated herein by reference. However, although these types of emulsions have found advantageous use in personal care products, these types of emulsions have not been used previously with agriculturally active compounds, which are typically present in emulsions at much higher levels than cosmetic active ingredients.

One example of an agricultural oil-in-water emulsion composition that is suitable for agriculturally active ingredients that are liquid or soluble in suitable solvents at relevant storage temperatures is disclosed in U.S. patent application Ser. No. 11/495,228, the disclosure of which is expressly incorporated by reference herein.

The present invention is related to agricultural compositions comprising an oil-in-water emulsion, the oil-in-water emulsion composition having an oil phase and water phase, the oil-in-water emulsion composition comprising an oil adapted to form oily globules having a mean particle diameter of less than 800 nanometers, at least one agriculturally active compound, at least one non-ionic lipophilic surface-active agent, at least one non-ionic hydrophilic surface-active agent, at least one ionic surface-active agent, at least one polymeric surface-active agent and water.

DETAILED DESCRIPTION

One embodiment of the present invention is a novel oil-in-water emulsion composition having an oil phase and water phase, the oil-in-water emulsion composition comprising:
 an oil adapted to form oily globules having a mean particle diameter of less than 800 nanometers;
 at least one polymeric surface active agent;
 at least one agriculturally active compound;
 at least one non-ionic lipophilic surface-active agent,
 at least one non-ionic hydrophilic surface-active agent;
 at least one ionic surface-active agent; and
 water.

The oil phase of the oil-in-water emulsion of the present invention utilizes either an agriculturally active compound which is in the form of an oil, or alternatively, an agriculturally active compound dissolved or mixed in an oil, to form the oily globules. An oil is by definition, a liquid which is not miscible with water. Any oil which is compatible with the agriculturally active compound may be used in the oil-in-water emulsions of the present invention. The term 'compatible' means that the oil will dissolve or mix uniformly with the agriculturally active compound and allow for the formation of the oily globules of the oil-in-water emulsion of the present invention. Exemplary oils include, but are not limited to short-chain fatty acid triglycerides, silicone oils, petroleum fractions or hydrocarbons such as heavy aromatic naphtha solvents, light aromatic naphtha solvents, hydrotreated light petroleum distillates, paraffinic solvents, mineral oil, alkylbenzenes, paraffinic oils, and the like; vegetable oils such as soy oil, rape seed oil, coconut oil, cotton seed oil, palm oil, soybean oil, and the like; alkylated vegetable oils and alkyl esters of fatty acids such as methyloleate and the like.

An agriculturally active compound is herein defined as any oil soluble compound, hydrophobic compound, or solid compound having a melting point of below about 95 degrees Celsius or less that shows some pesticidal or biocidal activity. It is understood to refer to the active compound per se when it is itself an oil or alternatively, the active compound dissolved in an oil of suitable polymeric modifier. Such compounds or pesticides include fungicides, insecticides, nematocides, miticides, termiticides, rodenticides, arthropodicides, herbicides, biocides and the like. Examples of such agriculturally active ingredients can be found in The Pesticide Manual, 12$^{th}$ Edition. Exemplary pesticides which can be utilized in the oil-in-water emulsion of the present invention include, but are not limited to, benzofuranyl methylcarbamate insecticides such as benfuracarb, and carbosulfan; oxime carbamate insecticides such as aldicarb; fumigant insecticides such as chloropicrin, 1,3-dichloropropene and methyl bromide; juvenile hormone mimics such as fenoxycarb; organophosphate insecticides such as dichlorvos; aliphatic organothiophosphate insecticides such as malathion and terbufos; aliphatic amide organothiophosphate insecticides such as dimethoate; benzotriazine organothiophosphate insecticides such as azinphos-ethyl and azinphos-methyl; pyridine organothiophosphate insecticides such as chlorpyrifos and chlorpyrifos-methyl; pyrimidine organothiophosphate insecticides such as diazinon; phenyl organothiophosphate insecticides such as parathion and parathion-methyl; pyrethroid ester insecticides such as bifenthrin, cyfluthrin, beta-cyfluthrin, cyhalothrin, gamma-cyhalothrin, lambda-cyhalothrin, cypermethrin, alpha-cypermethrin, beta-cypermethrin, fenvalerate, and permethrin; and the like.

Exemplary herbicides which can be used in the oil-in-water emulsion of the present invention include, but are not limited to: amide herbicides such as dimethenamid and dimethenamid-P; anilide herbicides such as propanil; chloroacetanilide herbicides such as acetochlor, alachlor, butachlor, metolachlor and S-metolachlor; cyclohexene oxime herbicides such as sethoxydim; dinitroaniline herbicides such as benfluralin, ethalfluralin, pendimethalin, and trifluralin; nitrile herbicides such asbromoxynil octanoate; phenoxyacetic herbicides such as 4-CPA, 2,4-D, 3,4-DA, MCPA, and MCPA-thioethyl; phenoxybutyric herbicides such as 4-CPB, 2,4-DB, 3,4-DB, and MCPB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as cyhalofop, fluazifop, fluazifop-P, haloxyfop, haloxyfop-R; pyridine herbicides such as aminopyralid, clopyralid, fluroxypyr, picloram, and triclopyr; triazole herbicides such as carfentrazone ethyl; and the like.

The herbicides can also generally be employed in combination with known herbicide safeners such as: benoxacor, cloquintocet, cyometrinil, daimuron, dichlormid, dicyclonon, dietholate, fenchlorazole, fenchlorazole-ethyl, fenclorim, flurazole, fluxofenim, furilazole, isoxadifen, isoxadifen-ethyl, mefenpyr, mefenpyr-diethyl, MG191, MON4660, R29148, mephenate, naphthalic anhydride, N-phenylsulfonylbenzoic acid amides and oxabetrinil.

Exemplary fungicides which can be used in the oil-in-water emulsion of the present invention include, but are not limited to, difenoconazole, dimethomorph, dinocap, diphenylamine, dodemorph, edifenphos, fenarimol, fenbuconazole, fenpropimorph, myclobutanil, oleic acid (fatty acids), propiconazole, tebuconazole and the like.

It is understood by those skilled in the art that any combination of agriculturally active compounds may also be used in the oil-in-water emulsion of the present invention as long as a stable and effective emulsion is still obtained.

The amount of agriculturally active ingredient within the oil-in-water emulsion will vary depending upon the actual active ingredient, the application of the agriculturally active ingredient and the appropriate application levels which are well known to those skilled in the art. Typically, the total amount of agriculturally active ingredient within the oil-in-water emulsion will be from about 1, generally from about 5, preferably from about 10, more preferably from about 15 and most preferably from about 20 to about 45, generally to about 40, preferably to about 35 and most preferably to about 30 weight percent based on the total weight of the oil-in-water emulsion.

The polymeric surface active agent or a combination of polymeric surface active agents may be included in the aqueous phase to stabilize the formulation in the presence of electrolytes. The polymeric surface active agent is typically an amphipathic block or graft copolymer with molecular weight greater than 1500. These consist of at least two chemically bound homopolymer components, one of which is soluble in the aqueous phase (hydrophilic part) of the formulation, while the other is normally insoluble (hydrophobic part). The latter, termed the anchor polymer, serves to attach the soluble species to the oil droplets. The soluble chains, which project away from the oil droplet surface into the aqueous phase together with the lamellar liquid crystal coating (to prevent oil droplet coalesce), sterically prevent oil droplets from approaching together, therefore stabilize oil-in-water emulsions. The polymeric surface active agent typically has a Hydrophilic Lipophilic Balance of greater than 12. Examples of suitable polymeric surface active agents may include Toximul 8323, Soprophor 796P, and Atlas G5000.

Examples of such agriculturally active ingredients that may be used in the oil-in-water emulsion composition of the present disclosure include Fluroxypyr Meptyl, Chloropyrifos, Chlorpyrifos methyl, Trifluralin, Cyhalofop butyl, Ethalfluralin, Benfluralin, Myclobutanil, Acequinocyl, Alpha-cypermethrin, Amitraz, Bensultap, Beta-cyfluthrin, Beta-cypermethrin, Bifenox, Bifenthrin, Bioresmethrin, Bromoxynil Octanoate, Butralin, Cyflufenamid, Cyfluthrin, Cypermethrin, Diclofop-methyl, Dicofol, Esfenvalerate, Ethalfluralin, Etofenprox, Fenazaquin, Fenoxaprop-P-ethyl, Fenpropathrin, Fenvalerate, Flumiclorac-pentyl, Fluoroglycofen-ethyl, Flurazole, Haloxyfop-etotyl, Indoxacarb, Lambda-cyhalothrin, Metamifop, Methoxychlor, Oxyfluorfen, Pendimethalin, Permethrin, Propaquizafop, Pyributicarb, Quizalofop-P-ethyl, Trifloxystrobin, Bromophos, Fenoxaprop-ethyl, Fluazolate, Nitrofen, and Profluralin.

The components of the oil-in-water emulsion are combined using a process described below to produce oily globules having a lamellar liquid crystal coating. The lamellar liquid crystal coating is an extremely fine mono- or oligolamellar layer. Oligolamellar layer is understood to refer to a layer comprising from 2 to 5 lipid lamellae. This lamellar liquid crystal coating can be detected by Transmission Electronic Microscopy after cryofracture or negative stain, X-Ray diffraction or Optical Microscopy under polarized light. Terms and structure of lamellar crystal liquid phase are well defined in "The Colloidal Domain" second edition, by D. Fennell Evans and H. Wennerstrom, Wiley-VCH (1999), pages 295-296 and 306-307. The oligolamellar layer is comprised of the non-ionic lipophilic, non-ionic hydrophilic, and ionic surface-active agents, as stated previously. Preferably, the lipophilic surface-active agent and the hydrophilic surface-active agent each contain at least one optionally saturated and/or branched fatty hydrocarbon chain having more than 12 carbon atoms, preferably from 16 to 22 carbon atoms.

Preferably, the lipophilic surface-active agent has an HLB between about 2 and about 5. HLB is a standard term known to those skilled in the art and refers to Hydrophilic Lipophilic Balance which identifies the emulsifier's solubility in water or oil.

Lipophilic describes the ability of a material to dissolve in a fat-like solvent or lipid. The lipophilic surface-active agent is typically selected from optionally ethoxylated mono- or polyalkyl ethers or esters of glycerol or polyglycerol, mono- or polyalkyl ethers or esters of sorbitan (optionally ethoxylated), mono- or polyalkyl ethers or esters of pentaerythritol, mono- or polyalkyl ethers or esters of polyoxyethylene, and mono- or polyalkyl ethers or esters of sugars. Examples of lipophilic surface-active agents include, but are not limited to sucrose distearate, diglyceryl distearate, tetraglyceryl tristearate, decaglyceryl decastearate, diglyceryl monostearate, hexaglyceryltristearate, decaglyceryl pentastearate, sorbitan monostearate, sorbitan tristearate, diethylene glycol monostearate, the ester of glycerol and palmitic and stearic acids, polyoxyethylenated monostearate 2 EO (containing 2 ethylene oxide units), glyceryl mono- and dibehenate and pentaerythritol tetrastearate.

Hydrophilic describes the affinity of a material to associate with water. The hydrophilic surface-active agent typically has a HLB of from about 8 to about 12 and are typically selected from mono- or polyalkyl ethers or esters of polyethoxylated sorbitan, mono- or polyalkyl ethers or esters of polyoxyethylene, mono- or polyalkyl ethers or esters of polyglycerol, block copolymers of polyoxyethylene with polyoxypropylene or polyoxybutylene, and mono- or polyalkyl ethers or esters of optionally ethoxylated sugars. Examples of hydrophilic surface-active agents include, but are not limited to polyoxyethylenated sorbitan monostearate 4 EO, polyoxyethylenated sorbitan tristearate 20 EO, polyoxyethylenated sorbitan tristearate 20 EO, polyoxyethylenated monostearate 8 EO, hexaglyceryl monostearate, polyoxyethylenated monostearate 10 EO, polyoxyethylenated distearate 12 EO and polyoxyethylenated methylglucose distearate 20 EO.

In addition to the polymeric, lipophilic, and hydrophilic surface-active agents, an ionic surface-active agent also comprises the oligolamellar layer of the lamellar liquid crystal coating.

Ionic surface-active agents which can be used in the oil-in-water emulsion of the present invention include (a) neutralized anionic surface-active agents, (b) amphoteric surface-active agents, (c) alkylsulphonic derivatives and (d) cationic surface-active agents.

Neutralized anionic surface-active agents (a) include, but are not limited to, for example:

alkali metal salts of dicetyl phosphate and dimyristyl phosphate, in particular sodium and potassium salts;

alkali metal salts of cholesteryl sulphate and cholesteryl phosphate, especially the sodium salts;

lipoamino acids and their salts, such as mono- and disodium acylglutamates, such as the disodium salt of N-stearoyl-L-glutamic acid, the sodium salts of phosphatidic acid;

phospholipids; and the mono- and disodium salts of acylglutamic acids, in particular N-stearoylglutamic acid.

Anionic surface-active agents chosen from alkyl ether citrates and mixtures thereof which can be used in the oil-in-water emulsions of the present invention are disclosed in U.S. Pat. No. 6,413,527, which is incorporated herein by reference. Alkyl ether citrates include monoesters or diesters formed by citric acid and at least one oxyethylenated fatty alcohol comprising a saturated or unsaturated, linear or branched alkyl chain having from 8 to 22 carbon atoms and comprising from 3 to 9 oxyethylene groups, and mixtures thereof. These citrates can be chosen, for example from the mono- and diesters of citric acid and of ethoxylated lauryl alcohol comprising from 3 to 9 oxyethylene groups. The alkyl ether citrates are preferably employed in the neutralized form at a pH of about 7. Neutralization agents can being chosen from inorganic bases, such as sodium hydroxide, potassium hydroxide or ammonia, and organic bases, such as mono,- di- and triethanolamine, aminomethyl-1,3-propanediol, N-methylglucamine, basic amino acids, such as arginine and lysine and mixtures thereof.

Amphoteric surface-active agents (b) include, but are not limited to phospholipids and especially phosphatidylethanolamine from pure soya.

Alkylsulphonic derivatives (c) include, but are not limited to compounds of the formula:

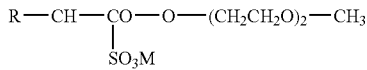

in which R represents the radicals $C_{16}H_{33}$ and $C_{18}H_{37}$, taken as a mixture or separately, and M is an alkali metal, preferably sodium.

Cationic surface-active agents (d) include but are not limited to surface-active agents as disclosed in U.S. Pat. No. 6,464,990, which is incorporated herein by reference. They are typically selected from the group of quaternary ammonium salts, fatty amines and salts thereof. The quaternary ammonium salts include, for example: those which exhibit the following formula:

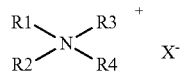

wherein the R1 to R4 radicals, which can be identical or different, represent a linear or branched aliphatic radical comprising from 1 to 30 carbon atoms or an aromatic radical, such as aryl or alkylaryl. The aliphatic radicals can comprise heteroatoms, such as oxygen, nitrogen, sulfur and halogens. The aliphatic radicals include alkyl, alkoxy, polyoxy($C_2$-$C_6$)alkylene, alkylamido, ($C_{12}$-$C_{22}$)alkylamido($C_2$-C6) alkyl, ($C_{12}$-$C_{22}$)alkyl acetate and hydroxyalkyl radicals comprising approximately from 1 to 30 carbon atoms; X is an anion selected from halides, phosphates, acetates, lactates, ($C_2$-$C_6$) alkyl sulfates, and alkyl- or alkylarylsulfonates. Preference is given, as quaternary ammonium salts to tetraalkylammonium chlorides, such as dialkyldimethylammonium and alkyltrimethylammonium chlorides in which the alkyl radical comprises approximately from 12 to 22 carbon atoms, in particularly behenyltrimethylammonium, distearyldimethylammonium, cetyltrimethylammonium and benzyldimethylstearylammonium chlorides, or alternatively, stearamidopropyldimethyl(myristyl acetate) ammonium chloride; imidazolinium quaternary ammonium salts, such as those of formula:

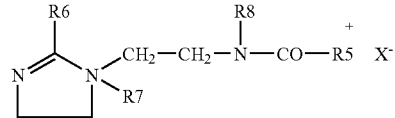

wherein R5 represents an alkenyl or alkyl radical comprising from 8 to 30 carbon atoms, for example derived from tallow fatty acids; R6 represents a hydrogen atom, an alkyl radical comprising from 1 to 4 carbon atoms or an alkenyl or alkyl radical comprising from 8 to 30 carbon atoms; R7 represents an alkyl radical comprising from 1 to 4 carbon atoms; R8 represents a hydrogen atom or an alkyl radical comprising from 1 to 4 carbon atoms; and X is an anion selected from the group of the halides, phosphates, acetates, lactates, alkyl sulfates, or alkyl, and alkylarylsulfonates. R5 and R6 preferably denote a mixture of alkenyl or alkyl radicals comprising from 12 to 21 carbon atoms, for example derived from tallow fatty acids, R7 preferably denotes a methyl radical and R8 preferably denotes hydrogen. Quaternary diammonium salts are also contemplated, such as propanetallowdiammonium dichloride.

Fatty amines include, but are not limited to those of formula:

wherein R9 is an optionally saturated and/or branched hydrocarbon chain, having between 8 and 30 carbon atoms, preferably between 10 and 24 carbon atoms; R10 and R11 are selected from H and an optionally saturated and/or branched hydrocarbon chain, having between 1 and 10 carbon atoms; preferably between 1 and 4 carbon atoms;

m is an integer between 1 and 10 and is preferably between 1 and 5; and n is either 0 or 1.

Examples of fatty amines include, but are not limited to, stearylamine, aminoethyl-ethanolamide stearate, diethylenetriamine stearate, palmitamidopropyldimethyl-amine, palmitamidopropyldiethylamine, palmitamidoethyldiethylamine, palmitamidoethyldimethylamine. Commercially available fatty amines include, but are not limited to, Incromine™ BB from Croda, Amidoamine™ MSP from Nikkol, and Lexamine™ series from Inolex, the Acetamine series from Kao Corp; Berol 380, 390, 453 and 455, and Ethomeen™ series from Akzo Nobel, and Marlazin™ L10, OL2, OL20, T15/2, T50 from Condea Chemie.

As described above, the surface-active agents form the lamellar liquid crystal coating of the oily globules suspended within the aqueous phase of the oil-in-water emulsion of the present invention. The amount of the three surface-active agents utilized in the oil-in-water emulsion of the present invention is typically from about 20, preferably from about 35 to about 65, preferably to about 55 weight percent of non-ionic lipophilic surface-active agent, from about 15, preferably from about 25 to about 50, preferably to about 40 weight percent of non-ionic hydrophilic surface-active agent and from about 5, preferably from about 10 to about 45, preferably to about 35 weight percent of ionic surface-active agent, based on the total combined weight of surface active agents. The amount of the polymeric surface-active agents utilized in the oil-in-water emulsion of the present invention is typically from about 0.1 to about 6 weight percent based on the total weight of oil-in-water emulsion. The coating of the oily globules comprises a total amount of hydrophilic surface-active agent, lipophilic surface-active agent and ionic surface-active agent to be between about 2 and about 20 percent by weight, based on the total weight of the oil-in-water emulsion. Preferably the total amount is from about 2.5, more preferably from about 3 to 10, more preferably to about 6 weight percent, based on the total weight of the oil-in-water emulsion.

The ratio of the total weight of the surface-active compounds (excluding polymeric surface-active compounds) to the total weight of oil is typically from 1:2.5 to 1:25.

The aqueous phase is typically water, for example, deionized water. The aqueous phase may also contain other additives such as compounds that lower the freezing point, for example alcohols, e.g. isopropyl alcohol and propylene glycol; pH buffering agents, for example alkali phosphates such as sodium phosphate monobasic monohydrate, sodium phosphate dibasic; biocides, for example Proxel GXL; and antifoams, for example octamethylcyclotetrasiloxane (Antifoam A from Dow Corning). Other additives and/or adjuvants can also be present in the aqueous phase as long as the stability of the oil-in-water emulsion is still maintained. Other additives also include water-soluble agriculturally active compounds.

The oil phase or the coated oily globules are from 5, preferably from 8 and more preferably from 10 to 50 percent, preferably to 45 and most preferably to 40 weight percent, based on the total weight of the oil-in-water emulsion composition. The oil/water ratio is typically less than or equal to 1.

Other additives and/or adjuvants can also be present within the oil-in-water emulsion of the present invention, as long as the stability and activity of the oil-in-water emulsion is still obtained. The oil-in-water emulsions of the present invention may additionally contain adjuvant surface-active agents to enhance deposition, wetting and penetration of the agriculturally active ingredient onto the target site, e.g. crop, weed or organism. These adjuvant surface-active agents may optionally be employed as a component of the emulsion in either the oil or water phase, or as a tank mix component; the use of and amount desired being well known by those skilled in the art. Suitable adjuvant surface-active agents include, but are not limited to ethoxylated nonyl phenols, ethoxylated synthetic or natural alcohols, salts of the esters or sulphosuccinic acids, ethoxylated organosilicones, ethoxylated fatty amines and blends of surface-active agents with mineral or vegetable oils.

The oil-in-water emulsion of the present invention can be prepared according to the process described in U.S. Pat. No. 5,925,364, the teachings of which are incorporated herein by reference. The agriculturally active ingredient or a combination of agriculturally active ingredients is first melted or dissolved into the solvent if desired, after which the nonionic surface-active agent(s) is dissolved into the mixture. The then mixture with the aqueous phase including the polymeric surface active agent and the ionic surface active is homogenized by cavitation using a high pressure homogenizer, to provide the small particle sized oily globules. The mean size of the coated oily globules is typically less than 800 nanometers, preferably less than 500 nanometers and most preferably about 200 nanometers, as determined using laser diffraction particle size analysis and scanning electron microscopy.

In one embodiment, the oil-in-water emulsion is prepared by:
1) melting or dissolving an agriculturally active ingredient(s) into an optional polymeric modifier and optionally a suitable solvent;
2) mixing an oil phase, comprising the lipophilic surfactant, the polymeric modifier (if used) containing the dissolved agriculturally active ingredient(s), the hydrophilic surfactant, an agriculturally active compound and optionally a suitable solvent and (B) an aqueous phase including the polymeric surface active agent and the ionic surface active agent to obtain a mixture; and
3) homogenizing the mixture by subjecting the mixture to cavitation.

In the first step, the mixture can be formed by conventional stirring, for example, using a high shear homogenizer rotating at a rate of approximately between 2000 and 7000 rpm for a time approximately between 5 and 60 minutes and at a temperature between approximately 20° C. and 95° C.

The homogenization can be performed by using a high pressure homogenizer operating at pressures between approximately 200 and 1000 bar as is well known to those skilled in the art. The process is performed by successive passages, generally from 1 to 12 passages, at a selected pressure; the mixture being returned to normal pressure between each passage. The homogenization of the second step may also be carried out under the action of ultrasound or alternatively by the use of a homogenizer equipped with a rotor-stator type head.

Another embodiment of the present invention is the use of the oil-in-water emulsion in agricultural applications to control, prevent or eliminate unwanted living organisms, e.g. fungi, weeds, insects, bacteria or other microorganisms and other pests. This would include its' use for protection of a plant against attack by a phytopathogenic organism or the treatment of a plant already infested by a phytopathogenic organism, comprising applying the oil-in-water emulsion composition, to soil, a plant, a part of a plant, foliage, flowers, fruit, and/or seeds in a disease inhibiting and phytologically acceptable amount. The term "disease inhibiting and phytologically acceptable amount" refers to an amount of a compound that kills or inhibits the plant disease for which control is desired, but is not significantly toxic to the plant. The exact concentration of active compound required varies with the fungal disease to be controlled, the type of formulations employed, the method of application, the particular plant species, climate conditions, and the like, as is well known in the art.

Additionally, the oil-in-water emulsions of the present invention are useful for the control of insects or other pests, e.g. rodents. Therefore, the present invention also is directed to a method for inhibiting an insect or pest which comprises applying to a locus of the insect or pest an oil-in-water emulsion comprising an insect-inhibiting amount of an agriculturally active compound for such use. The "locus" of insects or pests is a term used herein to refer to the environment in which the insects or pests live or where their eggs are present, including the air surrounding them, the food they eat, or objects which they contact. For example, insects which eat or contact edible or ornamental plants can be controlled by applying the active compound to plant parts such as the seed, seedling, or cutting which is planted, the leaves, stems, fruits, grain, or roots, or to the soil in which the roots are growing. It is contemplated that the agriculturally active compounds and oil-in-water emulsions containing such, might also be useful to protect textiles, paper, stored grain, seeds, domesticated animals, buildings or human beings by applying an active compound to or near such objects. The term "inhibiting an insect or pest" refers to a decrease in the numbers of living insects or pests, or a decrease in the number of viable insect eggs. The extent of reduction accomplished by a compound depends, of course, upon the application rate of the compound, the particular compound used, and the target insect or pest species. At least an inactivating amount should be used. The terms "insect or pest-inactivating amount" are used to describe the amount, which is sufficient to cause a measurable reduction in the treated insect or pest population, as is well known in the art.

The locus to which a compound or composition is applied can be any locus inhabited by an insect, mite or pest, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

Additionally, the present invention relates to the use of oil-in-water emulsions comprising agriculturally active compounds which are herbicides. The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include emerging seedlings and established vegetation.

Herbicidal activity is exhibited when they are applied directly to the locus of the undesirable plant thereof at any stage of growth or before emergence of the weeds. The effect observed depends upon the plant species to be controlled, the stage of growth of the plant, the particle size of solid components, the environmental conditions at the time of use, the specific adjuvants and carriers employed, the soil type, and the like, as well as the amount of chemical applied. These and other factors can be adjusted as is known in the art to promote selective herbicidal action. Generally, it is preferred to apply such herbicides post emergence to relatively immature undesirable vegetation to achieve the maximum control of weeds.

Another specific aspect of the present invention is a method of preventing or controlling pests such as nematodes, mites, arthropods, rodents, termites, bacteria or other microorganisms, comprising applying to a locus where control or prevention is desired a composition of the present invention which comprises the appropriate active compound such as a nematocide, miticide, arthropodicide, rodenticide, termiticide or biocide.

The actual amount of agriculturally active compound to be applied to loci of disease, insects and mites, weeds or other pests is well known in the art and can readily be determined by those skilled in the art in view of the teachings above.

The composition of the present invention surprisingly offers stable agricultural oil-in-water emulsions having low viscosity and long term shelf life. Additionally, the stable agricultural oil-in-water emulsions of the present invention can offer other surprising improvements, e.g. efficacy.

The following examples are provided to illustrate the present invention. The examples are not intended to limit the scope of the present invention and they should not be so interpreted. Amounts are in weight parts or weight percentages unless otherwise indicated.

EXAMPLES

These examples are provided to further illustrate the invention and are not meant to be construed as limiting.

As disclosed herein, all temperatures are given in degrees Celsius and all percentages are weight percentages unless otherwise stated.

In these examples, the process is performed using the following procedure:

The soybean oil modeling agriculturally active ingredient is mixed with non-ionic surfactants (the oil phase A). The phase A is poured into the aqueous phase B including polymeric surface active agents, ionic surface agent and NaCl, with stirring of 4000-8000 rpm provided by a Silverson L4RT high shear homogenizer fitted with a square hole high shear screen. Stirring and temperature conditions are maintained for 10 minutes.

The mixture is then introduced into a Niro Soavi high pressure 2-stage homogenizer of type Panda 2K, which is adjusted to a pressure of 1000 bar for 1 to 12 successive passages.

A stabilized oil-in-water emulsion is thus obtained, the oily globules of which have a mean diameter of typically around 200 nm.

Example 1

Effect of Polymeric Surface Active Agent on Oil-in-Water Emulsion Stability in Salt Environment In order to illustrate the effect of polymeric surface active agents on oil-in-water emulsion stability in a salt environment, a model emulsion including soybean oil was developed as shown in Table 1.

TABLE 1

| 30% soybean oil emulsion | |
|---|---|
| | wt % |
| Oil phase | |
| Soybean Oil | 30.0 |
| Brij 72 | 2.0 |
| Tween 61 | 1.5 |

TABLE 1-continued

30% soybean oil emulsion

| | wt % |
|---|---|
| Aqueous phase | |
| Cedepal TD-407 | 0.68 |
| Propylene Glycol | 10 |
| Water | 55.82 |

The developed model soybean oil emulsion was very stable. The emulsion did not experience any increase in particle size at Freeze/Thaw and 54° C. over a 2 week period.

Next, a similar emulsion was made including 0.01 M sodium chloride. The formulation is listed in Table 2.

TABLE 2

30% soybean oil EcoZome with 0.01M NaCl

| | wt % |
|---|---|
| Oil phase | |
| Soybean Oil | 30.0 |
| Brij 72 | 2.0 |
| Tween 61 | 1.5 |
| Aqueous phase | |
| Cedepal TD-407 | 0.68 |
| NaCl | 0.06 (0.01M) |
| Propylene Glycol | 10 |
| Water (balanced ingredient) | 55.8 |

The soybean oil emulsion with 0.01 M NaCl was unstable. Phase separation occurred after two weeks storage at 54° C.

Two exemplary polymeric surfactants were chosen to add to the above formulation to improve stabilization at salt conditions. Table 3 and Table 4 show two exemplary formulations at salt conditions.

TABLE 3

30% soybean oil EcoZome with 4% Toximul 8223 and 0.4M NaCl

| | wt % |
|---|---|
| Oil phase | |
| Soybean Oil | 30.0 |
| Brij 72 | 2.0 |
| Tween 61 | 1.5 |
| Aqueous phase | |
| Cedepal TD-407 | 0.68 |
| Toximul 8223 | 4 |
| NaCl | 2.34 (0.4M) |
| Propylene Glycol | 10 |
| Water (balanced ingredient) | 49.48 |

TABLE 4

30% Soybean Oil EcoZome with 0.5% Soprophor 796/P and 0.2M NaCl

| | wt % |
|---|---|
| Oil phase | |
| Soybean Oil | 30.0 |
| Brij 72 | 2.0 |
| Tween 61 | 1.5 |

TABLE 4-continued

30% Soybean Oil EcoZome with 0.5% Soprophor 796/P and 0.2M NaCl

| | wt % |
|---|---|
| Aqueous phase | |
| Cedepal TD-407 | 0.68 |
| Soprophor 796/P | 0.5 |
| NaCl | 1.2 (0.2M) |
| Propylene Glycol | 10 |
| Water (balanced ingredient) | 54.12 |

Both samples were stable after 2 weeks storage at 54° C. and Freeze/Thaw (temperature cycled from 40° C. to −10° C. every 24 hours). The addition of an polymeric surface active agents improved the salt tolerant property of the emulsion by about 40 times.

Example 2

Effect of Salt Concentration on Emulsion Stabilized by Polymeric Surfactant

The effect of salt concentration on an emulsion stabilized by a polymeric surfactant was investigated at a model formulation shown in Table 5. The salt concentration was varied at 0.4 M, 0.5M and 0.6M.

TABLE 5

30% soybean oil ecozome with 4% Toximul 8223 and 0.4M, 0.5M & 0.6M NaCl

| | wt % |
|---|---|
| Oil phase | |
| Soybean Oil | 30.0 |
| Brij 72 | 2.0 |
| Tween 61 | 1.5 |
| Aqueous phase | |
| Cedepal TD-407 | 0.68 |
| Toximul 8223 | 4 |
| NaCl | 2.34 (0.4M); 2.92 (0.5M); 3.51 (0.6M) |
| Propylene Glycol | 10 |
| Water | balanced ingredient |

It was found that at 0.4M NaCl concentration, the sample was stable after 2 weeks at 54° C. and Freeze/Thaw (temperature cycled from 40° C. to −10° C. every 24 hours), while at higher salt concentrations (0.5 M & 0.6M), samples were stable after 2 weeks at 54° C., but oil droplets started growing after 2 weeks at F/T.

Example 3

Effect of Polymeric Surfactant Concentration on the Stability of Emulsion at Salt Environment The effect of polymeric surfactant concentration on the stability of EcoZomes at salt environment was studied using a model system shown in Table 6.

TABLE 6

30% soybean oil ecozome with 0.4M
NaCl & 0.5%, 2% & 4% Soprophor 796/P

| | wt % |
|---|---|
| Oil phase | |
| Soybean Oil | 30.0 |
| Brij 72 | 2.0 |
| Tween 61 | 1.5 |
| Aqueous phase | |
| Cedepal TD-407 MFLD | 0.68 |
| Soprophor 796/P | 0.5; 2; 4 |
| NaCl | 2.34 (0.4M) |
| Propylene Glycol | 10 |
| Water | balanced ingredient |

In this example, the salt concentration was fixed at 0.4M, while the concentration of Soprophor 796/P was varied from 0.5% to 4%. It was found that there may exist an optimized polymer surface active agent concentration. At 2% of Soprophor 796/P concentration, the emulsion was relatively stable at both 54° C. and F/T conditions, while increasing or decreasing polymeric surface active agent concentration showed less stable behavior including phase separation in both samples after two weeks in storage.

What is claimed is:

1. A composition, comprising an oil-in-water emulsion including an oil phase and water phase, the oil-in-water emulsion comprising:
    at least one salt, wherein said salt is not a surfactant;
    at least one agriculturally active compound;
    at least one non-ionic lipophilic surface-active agent;
    at least one non-ionic hydrophilic surface-active agent;
    at least one ionic surface-active agent; and
    at least one polymeric surface active agent, wherein the polymeric surface active agent is an amphipathic block or graft copolymer with a molecular weight greater than 1500 and has an Hydrophilic Lipophilic Balance greater than 12;
    wherein the oil-in-water emulsion is from about 10 to about 40 weight percent total oil phase, from about 0.5 to about 4 weight percent polymeric surface active agent, from about 15 to about 40 weight percent agriculturally active compound, from about 1.2 to about 3.51 weight percent salt, and a total amount of from about 3 to 6 weight percent of the non-ionic lipophilic surface-active agent, non-ionic hydrophilic surface-active agent, and ionic surface-active agent, based on a total weight of the oil-in-water emulsion.

2. The composition of claim 1 wherein the non-ionic lipophilic surface-active agent has a Hydrophilic Lipophilic Balance of between 2 and 5.

3. The composition of claim 2, wherein the non-ionic lipophilic surface-active agent is selected from the group consisting of optionally ethoxylated mono- or polyalkyl ethers or esters of glycerol or polyglycerol, optionally ethoxylated mono- or polyalkyl ethers or esters of sorbitan, mono- or polyalkyl ethers or esters of pentaerythritol, mono- or polyalkyl ethers or esters of polyoxyethylene, and mono- or polyalkyl ethers or esters of sugars.

4. The composition of claim 3, wherein the non-ionic lipophilic surface-active agent is selected from the group consisting of sucrose distearate, diglyceryl distearate, tetraglyceryl tristearate, decaglyceryl decastearate, diglyceryl monostearate, hexaglyceryltristearate, decaglyceryl pentastearate, sorbitan monostearate, sorbitan tristearate, diethylene glycol monostearate, the ester of glycerol and palmitic and stearic acids, polyoxyethylenated monostearate 2 EO (containing 2 ethylene oxide units), glyceryl mono- and dibehenate and pentaerythritol tetrastearate.

5. The composition of claim 1, wherein the non-ionic hydrophilic surface-active agent has an Hydrophilic Lipophilic Balance between 8 and 12.

6. The composition of claim 5, wherein the non-ionic hydrophilic surface-active agent is selected from the group consisting of mono- or polyalkyl ethers or esters of polyethoxylated sorbitan, mono- or polyalkyl ethers or esters of polyoxyethylene, mono- or polyalkyl ethers or esters of polyglycerol, block copolymers of polyoxyethylene with polyoxypropylene or polyoxybutylene, and mono- or polyalkyl ethers or esters of optionally ethoxylated sugars.

7. The composition of claim 6, wherein the non-ionic hydrophilic surface-active agent is selected from the group consisting of polyoxyethylenated sorbitan monostearate 4 EO, polyoxyethylenated sorbitan tristearate 20 EO, polyoxyethylenated sorbitan tristearate 20 EO, polyoxyethylenated monostearate 8 EO, hexaglyceryl monostearate, polyoxyethylenated monostearate 10 EO, polyoxyethylenated distearate 12 EO and polyoxyethylenated methylglucose distearate 20 EO.

8. The composition of claim 1, wherein the ionic surface-active agent is selected from the group consisting of (a) neutralized anionic surface-active agents, (b) amphoteric surface-active agents, (c) alkylsulphonic derivatives and (d) cationic surface-active agents.

9. The composition of claim 8, wherein the ionic surface-active agent is selected from the group consisting of: alkali metal salts of dicetyl phosphate and dimyristyl phosphate; alkali metal salts of cholesteryl sulphate and cholesteryl phosphate; lipoamino acids and their salts, such as mono- and disodium acylglutamates; the sodium salts of phosphatidic acid; phospholipids; the mono- and disodium salts of acylglutamic acids; and alkyl ether citrates.

10. The composition of claim 8, wherein the ionic surface-active agent is a phospholipid.

11. The composition of claim 8, wherein the ionic surface-active agent is an alkylsulphonic derivative.

12. The composition of claim 8, wherein the ionic surface-active agent is selected from the group consisting of quaternary ammonium salts, fatty amines and salts thereof.

13. The composition of claim 1, wherein the agriculturally active compound is selected from a group consisting of fungicides, insecticides, nematocides, miticides, biocides, termiticides, rodenticides, arthropodicides, and herbicides.

14. A method of controlling or preventing fungal attack, comprising applying a composition of claim 13 to the fungus, soil, plant, root, foliage, seed or locus in which the infestation is to be prevented or controlled.

15. A method of inhibiting insects comprising applying to a locus where control or prevention is desired a composition of claim 13.

16. A method of preventing or controlling unwanted vegetation comprising applying to a locus where control or prevention is desired a composition of claim 13.

17. A method of preventing or controlling nematodes, comprising applying to a locus where control or prevention is desired a composition of claim 13.

18. A method of preventing or controlling mites, comprising applying to a locus where control or prevention is desired a composition of claim 13.

19. A method of preventing or controlling arthropods, comprising applying to a locus where control or prevention is desired a composition of claim 13.

20. A method of controlling bacteria comprising applying to a locus where control is desired a composition of claim 13.

21. A method of preventing or controlling rodents, comprising applying to a locus where control or prevention is desired a composition of claim 13.

22. A method of preventing or controlling termites, comprising applying to a locus where control or prevention is desired a composition of claim 13.

23. The composition of claim 1, wherein the oil-in-water emulsion is about 2.34 to about 3.51 weight percent salt.

24. The composition of claim 1, wherein the oil-in-water emulsion is about 2 weight percent polymeric surface active agent.

25. The composition of claim 1, wherein the at least one salt is sodium chloride.

* * * * *